United States Patent
Heismann

(10) Patent No.: US 7,319,739 B2
(45) Date of Patent: Jan. 15, 2008

(54) IMAGING METHOD BASED ON TWO DIFFERENT X-RAY SPECTRA

(75) Inventor: Björn Heismann, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 17 days.

(21) Appl. No.: 10/549,269

(22) PCT Filed: Mar. 2, 2004

(86) PCT No.: PCT/EP2004/002094

§ 371 (c)(1),
(2), (4) Date: Sep. 13, 2005

(87) PCT Pub. No.: WO2004/080308

PCT Pub. Date: Sep. 23, 2004

(65) Prior Publication Data

US 2006/0269043 A1    Nov. 30, 2006

(30) Foreign Application Priority Data

Mar. 14, 2003  (DE) ............................... 103 11 628

(51) Int. Cl.
*G01N 23/04* (2006.01)
(52) U.S. Cl. ............................................. 378/62; 378/5
(58) Field of Classification Search .............. 378/5, 378/8, 62, 54, 4
See application file for complete search history.

(56) References Cited

U.S. PATENT DOCUMENTS

| | | | |
|---|---|---|---|
| 4,149,081 A | * | 4/1979 | Seppi ............................ 378/5 |
| 4,247,774 A | | 1/1981 | Brooks |
| 4,662,379 A | | 5/1987 | Macovski |
| 4,709,382 A | * | 11/1987 | Sones .......................... 378/62 |
| 2004/0223585 A1 | | 11/2004 | Heismann et al. |

FOREIGN PATENT DOCUMENTS

DE    44 33 564 A1    4/1996

(Continued)

OTHER PUBLICATIONS

W. Kalender et al., "Materialselektive Bildgebung und Dichtemessung mit der Zwei-Spektren-Methode i. Grundlagen und Methodik", Digit. Bilddiagn. 7, 1987, 66-72, Georg Thieme Verlag, Stuttgart.

(Continued)

*Primary Examiner*—Hoon Song
(74) *Attorney, Agent, or Firm*—Harness, Dickey & Pierce, PLC

(57) ABSTRACT

A method is for imaging examination of an examination object. A contrast agent is administered to the object to be examined. At least two spatial distributions of X-ray attenuation values are determined, the values respectively representing the local X-ray attenuation coefficients or a quantity which is linearly dependent on the same. The two spatial distributions include at least one first attenuation value distribution and one second attenuation value distribution having determinations based on different X-ray spectrums. By evaluating the two attenuation value distributions, a spatial distribution of at least one predefined atomic number value or a spatial distribution of a non-predefined atomic number value in the object to be examined is determined, the spatial distribution containing information about the distribution of the administered contrast agent in the object to be examined. The spatial atomic number distribution is used to represent the contrast agent in the image.

18 Claims, 4 Drawing Sheets

FOREIGN PATENT DOCUMENTS

| | | |
|---|---|---|
| DE | 100 02 939 C1 | 9/2001 |
| DE | 101 27 267 A1 | 12/2002 |
| DE | 101 43 131 A1 | 4/2003 |
| EP | 0 041 752 A1 | 12/1981 |
| EP | 0 385 505 A2 | 9/1990 |
| WO | WO-97/24069 A1 | 7/1997 |
| WO | WO-00/16811 A2 | 3/2000 |

OTHER PUBLICATIONS

International Search Report.
International Preliminary Examination Report.
German Translation Aid.
Chinese Office Action corresponding to Chinese Patent Application No. 20048001240.8.

* cited by examiner

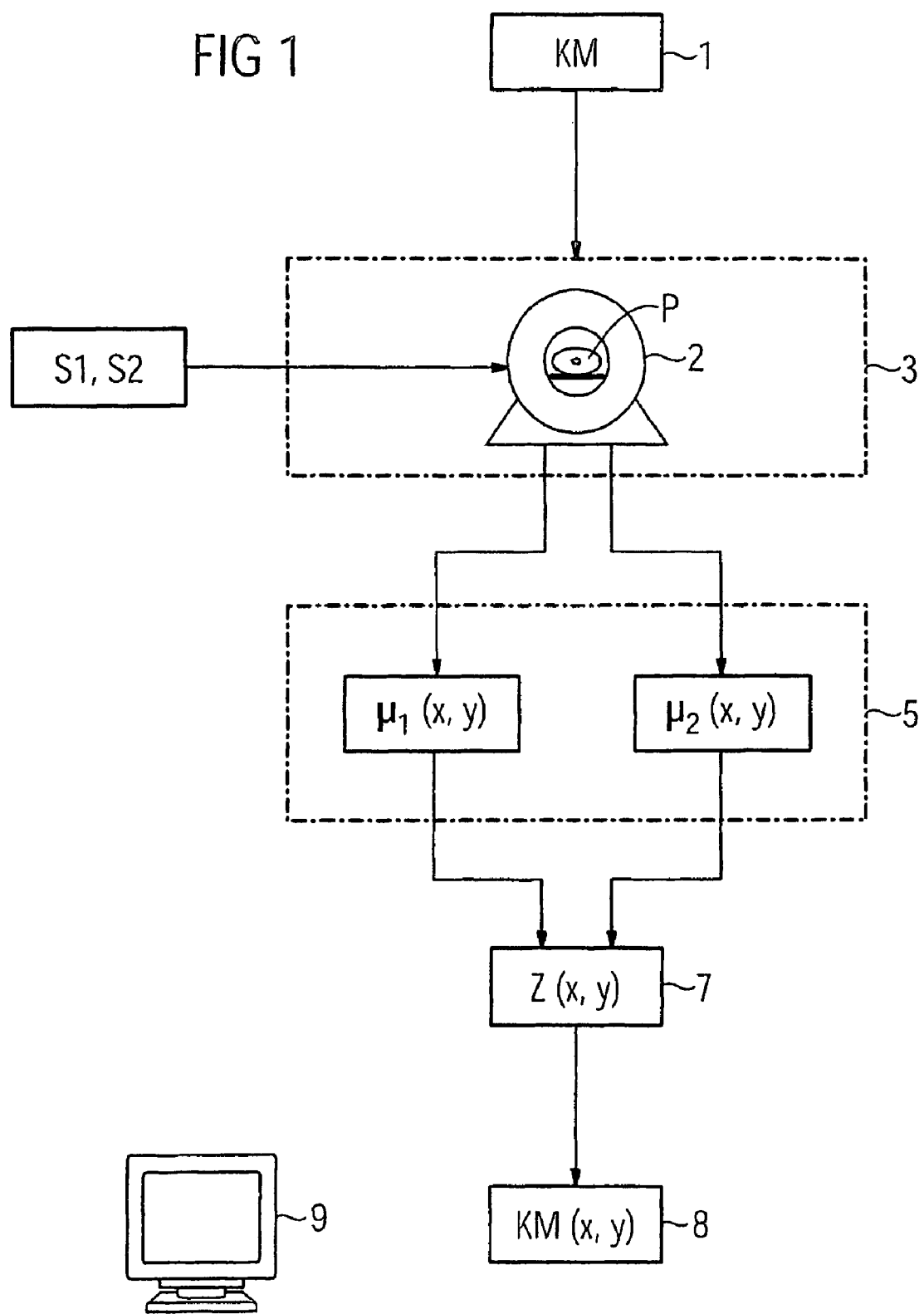

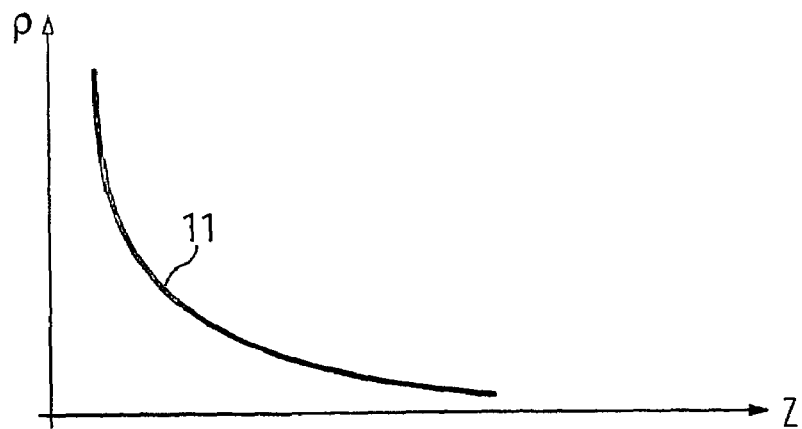
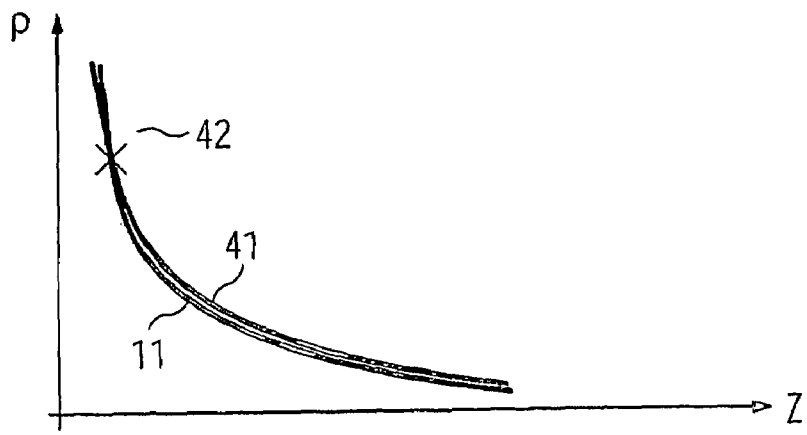

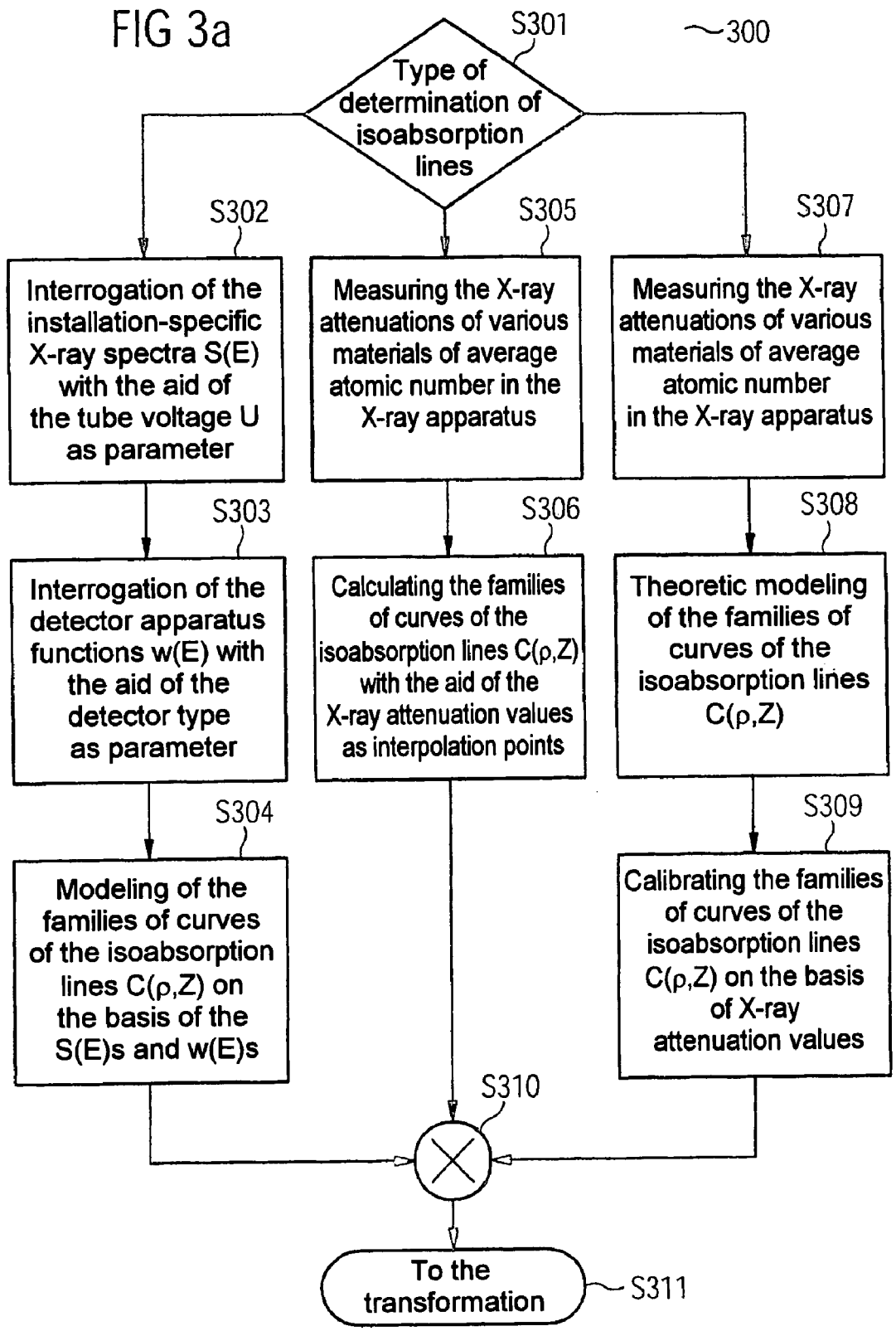

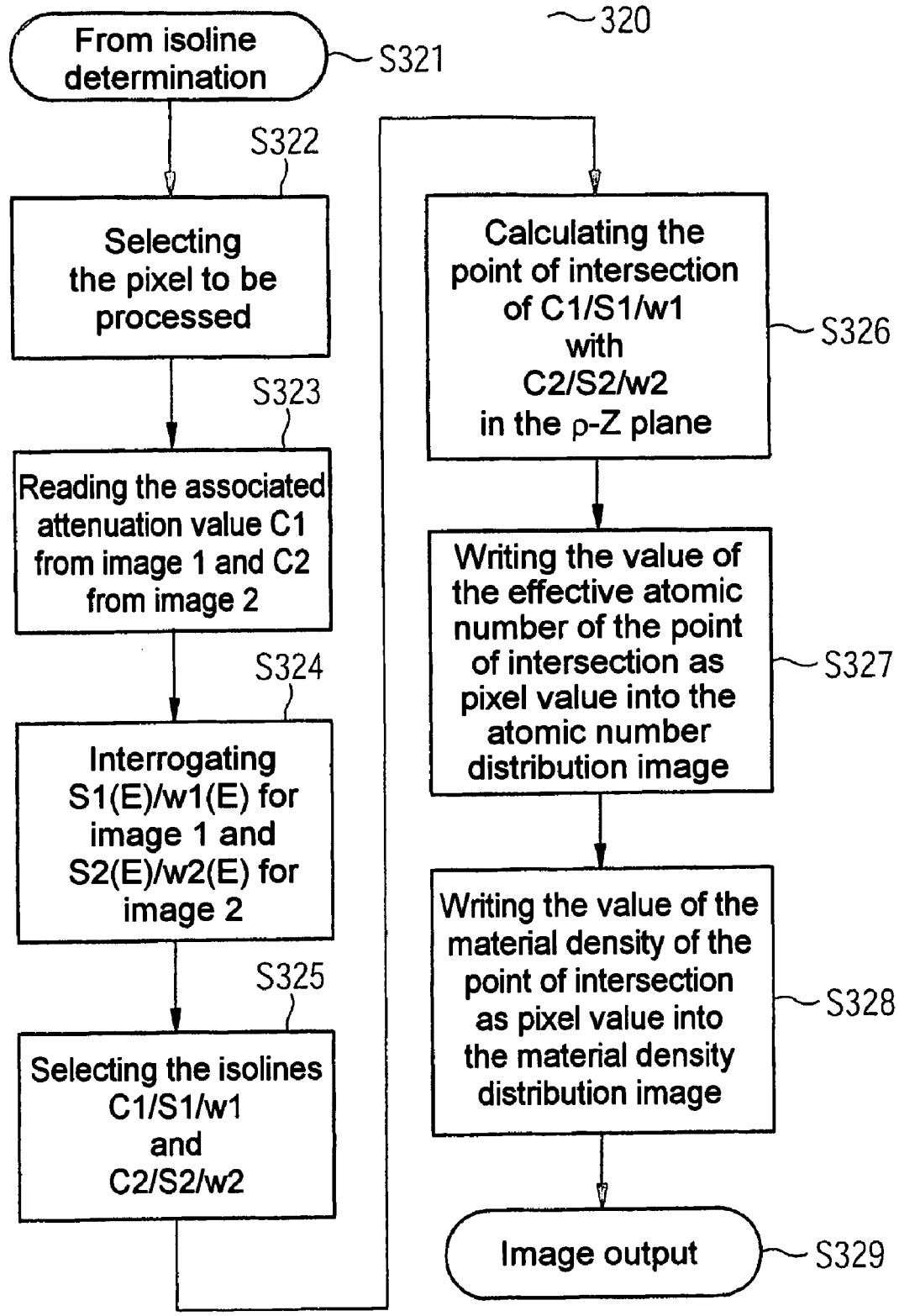

IMAGING METHOD BASED ON TWO DIFFERENT X-RAY SPECTRA

This application is the national phase under 35 U.S.C. § 371 of PCT International Application No. PCT/EP2004/002094 which has an International filing date of Mar. 2, 2004, which designated the United States of America and which claims priority on German Patent Application number DE 103 11 628.1 filed Mar. 14, 2003, the entire contents of which are hereby incorporated herein by reference.

FIELD

The invention generally relates to a method for imaging examination of an examination object that for medical purposes may be, in particular, a patient. The method is suitable in particular for application in the course of a tomography method or for application in an imaging examination device capable of tomography, for example in an X-ray computed tomography unit.

BACKGROUND

Contrast agents are known, for example, from DE 44 33 564 A1, WO 00/16811 or DE 100 02 939 C1.

The result of radiographic methods such as, for example, computed tomography, mammography, angiography, X-ray inspection technology or comparable methods, is firstly the representation of the attenuation of an X-ray along its path from the X-ray source to the X-ray detector (projection image). This attenuation is caused by the transradiated media or materials along the beam path, and so the attenuation can also be understood as a line integral over the attenuation coefficient of all pixels along the beam path. Particularly in the case of tomography methods, for example in X-ray computed tomography, so-called construction methods can be used to calculate backward from the projected attenuation data to the attenuation coefficients ($\mu$) of the individual pixels, and thus to achieve a substantially more sensitive examination than from purely evaluating the projection images.

Instead of the attenuation coefficient, use is generally made for the purpose of representing the attenuation distribution of a value normalized to the attenuation coefficient of water, the so-called CT number. This is calculated from an attenuation coefficient $\mu$, currently determined by measurement, and the reference attenuation coefficient $\mu_{H_2O}$ using the following equation:

$$C = 1000 \times \frac{\mu - \mu_{H_2O}}{\mu_{H_2O}} [HU], \quad (1)$$

where the CT number C is in Hounsfield [HU]. A value of $C_{H_2O}=0$ HU is used for water, and for air a value $C_L=-1000$ HU.

Since both representations can be transformed into, or are equivalent to, one another, the generally selected term of attenuation value or attenuation coefficient designates below both the attenuation coefficient $\mu$ and the CT value. Furthermore, the terms material and tissue are used exchangeably in the context of the subject of this description of embodiments of the invention. It is assumed that in the context of a medically indicated examination a material can be an anatomical tissue, or conversely for material and safety testing a tissue is understood to be any desired material of an examination object.

Although the informativeness of an image based on the local attenuation coefficient ($\mu$) is clearly enhanced, problems can nevertheless arise with interpreting an image in the individual case. Specifically, a locally increased attenuation value can be ascribed either to materials of higher atomic number such as, for example, calcium in the skeleton or iodine in a contrast agent, or to an increased soft part density such as, for example, in the case of a pulmonary nodule. The local attenuation coefficient $\mu$ at the location $\vec{r}$ is dependent on the X-ray energy E irradiated into the tissue and/or material and the local tissue and/or material density $\rho$ in accordance with the following equation:

$$\mu = \mu(E, \vec{r}) = \frac{\mu}{\rho}(E, Z) \times \rho(\vec{r}), \quad (2)$$

with the energy-dependent and material-dependent mass attenuation coefficient $$\frac{\mu}{\rho}(E, Z)$$

and the (effective) atomic number Z.

The energy-dependent X-ray absorption of a material as determined by its effective atomic number Z is therefore superimposed on the X-ray absorption influenced by the material density $\rho$. Materials and/or tissue of different chemical and physical composition can therefore exhibit identical attenuation values in the X-ray image. Conversely, by contrast, it is not possible to deduce the material composition of an examination object from the attenuation value of an X-ray picture.

Methods for representing characteristic values of materials are required in order to solve this problem. In conjunction with computer-aided tomography methods, it is known, for example from U.S. Pat. No. 4,247,774, to use mutually different X-ray spectra or X-quantum energies to produce an image.

Such methods are generally denoted as dual-spectrum CT. They utilize the energy dependence, governed by atomic number, of the attenuation coefficient $\mu$, that is to say they are based on the effect that materials and tissue of higher atomic number absorb low-energy X-radiation substantially more intensely than do materials and/or tissues of lower atomic number.

By contrast, in the case of higher X-ray energies the attenuation values are equal and are largely a function of material density. In the case of dual-spectrum CT, the differences in the images recorded for different X-ray tube voltages are then calculated, for example.

Unless otherwise specified, in the context of this description of embodiments, the term atomic number is used not in the strict sense as referring to elements. Instead it denotes an effective atomic number of a tissue, or material, that is calculated from the chemical atomic numbers and atomic weights of the elements participating in the structure of the tissue and/or material.

Even more specific statements are arrived at when, in addition, the method of so-called base material decomposition is applied in the case of X-ray pictures, for example as described in W. Kalender et al. in "Materialselektive Bildgebung und Dichtemessung mit der Zwei-Spektren-Methode, I. Grundlagen und Methodik" ["Material-selective imaging and density measurement with the dual-spectrum method, I. fundamentals and methodology"], W. Kalender, W. Bautz, D. Felsenberg, C. Süß and E. Klotz, Digit. Bilddiagn. 7, 1987, 66-77, Georg Thieme Verlag.

In this method, the X-ray attenuation values of an examination object are measured with the aid of X-ray beams of lower and higher energy, and the values obtained are compared with the corresponding reference values of two base materials such as, for example, calcium (for skeletal material) and water (for soft part tissues). It is assumed that each measured value can be represented as a linear superposition of the measured values of the two base materials. For example, a skeletal component and a soft tissue component can be calculated for each element of the pictorial representation of the examination object from the comparison with the values of the base materials, the result being a transformation of the original pictures into representations of the two base materials of skeletal material and soft part tissue.

The base material decomposition and the dual-spectrum method are therefore suitable for telling apart or distinguishing predefined anatomical structures or types of material in human and animal tissues having a sharply different atomic number.

German Patent Application with the application number 101 43 131 discloses a method whose sensitivity and informativeness further exceeds the base material decomposition and, for example, enables a functional CT imaging of high informativeness. It permits the calculation of the spatial distribution of the mean density $\rho(\vec{r})$ and of the effective atomic number $Z(\vec{r})$ from an evaluation of the spectrally influenced measured data of an X-ray apparatus. Very good contrasts are yielded thereby, for example with reference to the chemical and physical composition of the examination object. For example, the representation of the distribution of the atomic number in the tissue permits, inter alia, insight into the biochemical composition of an object being examined, contrasts based on chemical composition in organs previously represented as of homogeneous density, a quantitative determination of body constituents such as, for example, iodine or the like, and removal of instances of calcification by segmentation on the basis of the atomic number.

SUMMARY

An object of at least one embodiment of the present invention is to specify a method that provides new possibilities for improving sensitivity or for enhancing the informativeness in the case of imaging based on X-rays that depends on material or atomic number.

An object may be achieved according to at least one embodiment of the invention by a method for imaging examination of an examination object, in particular a patient, in which a) the examination object is administered a contrast agent,
b) thereafter, at least two spatial distributions of X-ray attenuation values are determined, which X-ray attenuation values in each case represent the local X-ray attenuation coefficient ($\mu(x,y)$), or a variable (C) linearly dependent thereon, the two spatial distributions comprising at least:
   a first attenuation value distribution determined on the basis of a first X-ray spectrum,
   a second attenuation value distribution determined on the basis of a second X-ray spectrum, differing from the first X-ray spectrum,
c) two attenuation value distributions are evaluated and a spatial distribution of one or more predefined atomic number values (Z; Z1, Z2, . . . ) or a spatial distribution (Z(x,y)) of non-predefined atomic number values present in the examination object is determined, which spatial distribution includes information relating to a distribution of the administered contrast agent in the examination object, and
d) the spatial atomic number distribution is used to represent the contrast agent by imaging.

At least one embodiment of the invention includes the idea that the use of contrast agents can improve functional imaging in X-ray computed tomography. In this context, contrast agents have so far been used merely in order, for example, to emphasize blood against its tissue background in terms of absorption. No evaluation of a selective nature in relation to material or tissue was made. At least one embodiment of the invention furthermore includes, inter alia, the finding that a difference in atomic number measurable by way of two different X-ray spectra can be attained by adding a contrast agent in a tolerable dose.

In the method according to at least one embodiment of the invention, an atomic number value of the contrast agent can be predefined. In particular, at least one embodiment of the method can be combined with the base material decomposition mentioned at the beginning.

The spatial atomic number distribution is preferably determined as a two- or three-dimensional field, the respective field value being a local atomic number value at the location represented by the relevant field. The method can, in particular, be combined with the method of the German Patent Application 101 43 131 mentioned at the beginning. The disclosure content of this patent application, in particular patent claims 1 and 7 there, is expressly incorporated into the present patent application by reference.

Moreover, in addition to the atomic number distribution a further two- or three-dimensional field is preferably determined whose field values respectively reproduce a local density value.

The use of the spatial atomic number distribution for imaging can be performed, for example, by displaying an image that displays only data from a specific atomic number interval—including the value of the atomic number of the contrast agent, for example—or beyond a specific atomic number limiting value. It is also possible to convert the measured atomic number values into a gray-value scale or color scale, in which case the value of the atomic number of the contrast agent can be emphasized, or be colored on its own, and to display this scale by imaging it. Such images can be superimposed on or subordinated to a conventional, non-functional attenuation image.

According to a particularly preferred example embodiment, the determined field having the atomic number values and the determined field having the density values are used for the purpose of calculating a local concentration or a local quantity of the contrast agent.

In the context of at least one embodiment of the invention, a contrast agent is understood as any agent that leads to an improvement in contrast or intensification in contrast in terms of absorption, that is to say in the X-ray image, after being added to the examination object, in particular after being injected into a patient. This covers both conventional contrast agents as administered, for example, into the blood vessels for perfusion measurements, in order to emphasize the blood vessels in the image. However, "contrast agents" are also understood as agents that are deposited or built up specifically or selectively; e.g. according to a key-lock principle, only at specific sites in the examination object, and thereby permit an organ function to be checked.

Such last known device(s)/thing(s)/method(s) can also be so-called markers or tracers. Such a marker is composed, for example, of a biological macromolecule, for example an antibody, a peptide or a sugar molecule, having a high affinity with the target structure to be examined, and of a contrast substance—which has additionally doped, for example—that can be effectively visualized in the X-ray image. The macromolecule serves, for example, as a so-called "metabolic marker" the effect of which is that the contrast agent, also denoted overall as metabolic marker, builds up either exclusively in specific regions, for example tumors, inflammations or other specific disease sites. Contrast agents are known, for example, from the documents named at the beginning.

Use is preferably made of a contrast agent having an atomic number of greater than 20 or greater than 40. The contrast agent has, in particular, an atomic number of less than 83 or less than 70.

Particularly advantageous contrast agents include gadolinium, iodine, ytterbium, dysposium, iron and/or bismuth.

According to a further advantageous refinement, the contrast agent includes an organic compound, in particular an aliphatic hydrocarbon, for example sugar, and/or an amino acid or a peptide.

The contrast agent can be designed for selective deposition at specific sites or in specific tissue parts of the examination object.

In an advantageous refinement, the contrast agent is added in a weight concentration from the range of $10^{-4}$ to $10^{-7}$, in particular from the range of $10^{-5}$ to $10^{-6}$.

The term "X-ray spectrum" used in the context of embodiments in this document has a more widely cast meaning than only the spectral distribution of an X-radiation emitted by the X-ray source of the apparatus. On the part of X-ray detectors, as well different spectral components of a radiation having different efficiencies can be converted, and thereby be weighted differently. The effective spectral distribution resulting therefrom is likewise denoted in this document as X-ray spectrum.

The two attenuation value distributions need not necessarily be recorded consecutively as two images with a different tube voltage. Since every X-ray tube emits a spectrum of a certain width, it is also possible given an appropriate spectrally selective configuration of an associated receiving unit, to record the two attenuation value distributions largely or completely simultaneously. It would be possible for this purpose, for example, to use filters that can be inserted into the beam path, and/or two separately present X-ray detector arrays.

In particular, a receiving unit is equipped for carrying out the method with an X-ray detector array that can select quantum energy.

Particularly with regard to a use of the method described in the German Patent Application 101 43 131 mentioned at the beginning, it is especially advantageous that a first functional dependence of a first attenuation value of the first attenuation value distribution of density and atomic number, and at least a second functional dependence of a second attenuation value, assigned to the first attenuation value, of the second attenuation value distribution of density and atomic number are determined, [and further that the spatial atomic number distribution—and optionally a spatial density distribution—is/are determined by comparing the first functional dependence with the second functional dependence and, if appropriate, with further functional dependences].

In this case, the determination of the functional dependence of the attenuation values on density and atomic number for at least one X-ray spectrum is preferably performed by way of reference measurement on a calibration sample or in the form of a simulation on the basis of a physical model.

According to another preferred refinement, the attenuation value distributions are converted into a distribution of the density and a distribution of the atomic number for each of the assigned attenuation values of the first attenuation value distribution and of the further attenuation value distributions on the basis of the determination of a value pair for density and atomic number, this being undertaken such that the value pair fulfills the specific functional dependences of the X-ray absorption on density and atomic number for the first X-ray spectrum and at least one further X-ray spectrum. If it is thereby possible for density and atomic number to be calculated easily for a pixel as interface of the functional dependences of the mutually assigned X-ray absorption values of the recorded distributions of the X-ray absorption values.

The first X-ray spectrum advantageously has quantum energy that in relation to the quantum energy of the second X-ray spectrum favors an X-ray absorption by the photoeffect such that a high resolution is obtained in the determination of the atomic numbers.

In a preferred example embodiment of the present invention, at least one operating parameter of the X-ray tube is varied in order to vary an X-ray spectrum for recording the examination object, the X-ray source emitting a first X-ray spectrum in a first operating state and emitting a second X-ray spectrum, different from the first X-ray spectrum, in a second operating state such that a rapid change between two X-ray spectra is rendered possible.

Furthermore, a variation of the detector characteristic is undertaken in order to vary an X-ray spectrum for recording the examination object, the X-ray detector converting spectral subregions of the X-radiation received from the X-ray source into mutually independent electric signals, and in the process permitting simultaneous recording of distributions of the X-ray absorption in the case of different X-ray spectra.

BRIEF DESCRIPTION OF THE DRAWINGS

The present invention is described in more detail below with the aid of example embodiments, reference being made to the following figures, in which:

FIG. 1 shows a flowchart of the method according to the invention in accordance with an example embodiment, FIG. 2 shows with the aid of an isoabsorption line the production of identical attenuation values μ for materials of different composition, FIG. 3a shows an example flowchart of a calculation method for determining isoabsorption lines as part of the method in accordance with FIG. 1, FIG. 3b shows an example flowchart of the transformation of the X-ray attenuation values to values of material density and atomic number as part of the method in accordance with FIG. 1, and FIG. 4 shows two isoabsorption lines of a type of tissue in the case of two different X-ray spectra.

DETAILED DESCRIPTION OF THE EXAMPLE EMBODIMENTS

An example embodiment of the method according to the invention is illustrated schematically as a flowchart in FIG. 1. In a first step 1, a patient P is administered a tracer or a contrast agent KM, for example by injection into the blood vessels or by swallowing. The patient P is then examined in an X-ray computed tomography unit 2 (merely indicated), specifically both with evaluation of a first X-ray spectrum S1 and—simultaneously or consecutively—with evaluation of a second X-ray spectrum S2 (second step 3) that are selected by appropriately setting the X-ray computed tomography unit 2.

Carrying out an image reconstruction (third step 5) on the basis of the raw data thus obtained results for each of the X-ray spectra S1, S2 in an attenuation value distribution, for example as a distribution $\mu_1(x,y)$ or $\mu_2(x,y)$ of the (linear) X-ray attenuation coefficient $\mu$ within a transaxial tomogram with coordinates x and y. In a fourth step 7, a computer-aided transformation of the distributions $\mu_1(x,y)$ and $\mu_2(x,y)$ of the X-ray attenuation coefficient into an atomic number distribution Z(x,y) takes place. The atomic number distribution Z(x,y) is used in a fifth step 8 to display a distribution of the contrast agent KM on a monitor 9.

An effective Z=7.52 results on the assumption of an exemplary injection of a Gd-based tracer with one Gd atom per $10^6$ water molecules (corresponding to approximately 9 ppm proportion by weight). Compared with the water value Z=7.42, this concentration can be verified with the aid of the method in accordance with an example embodiment of FIGS. 3a and 3b.

The method in accordance with an example embodiment of FIGS. 3a and 3b can be designed as part of the fourth step 7. Details of this method are described in the German Patent Application with the application number 101 43 131, the entire contents of which are incorporate herein by reference.

If the density distribution $\rho(x,y)$ is determined at the same time, the concentration of the tracer substance can be determined quantitatively given a known carrier material, for example resembling water.

The atomic number of the contrast agent KM should have as high a division as possible from the atomic number of the background material, typically water with Z=7.42.

As an alternative to the method in accordance with FIGS. 3a and 3b, it is also possible to use the conventional base material decomposition described at the beginning, in order to determine the spatial distribution of two or more previously defined atomic number values Z1, Z2, . . . in a transverse tomographic plane (x,y). Such a distribution can likewise be used to display the contrast agent KM in the image.

Explanations will firstly be given below with regard to explaining the method in accordance with FIGS. 3a and 3b: the isoabsorption line 11 of FIG. 2 connects all the value pairs $(\rho,Z)$ to an attenuation value $\mu$ or C, respectively, that is identical for a defined X-ray spectrum. The illustration of FIG. 1 makes it plain that information relating to the type and composition of a tissue or material can be derived in a fashion not based solely on the attenuation values of an X-ray image.

X radiation is attenuated with a different intensity by different materials and in a fashion dependent on the energy of the X radiation. This is to be ascribed to attenuation mechanisms that act differently for the various materials.

The effective atomic number Z of a specific tissue type, given the title of atomic number for simplicity in the context of this description, is calculated from the atomic numbers $Z_i$ of the elements participating in the structure, their atomic weights $A_i$ and their local material-equivalent densities $\rho_i$ for example as:

$$Z = \frac{\sum_i \frac{\rho_i}{A_i} \rho_i Z_i^{\frac{1}{3}}}{\sum_i \frac{\rho_i}{A_i} \rho_i} \quad (3)$$

The result is $Z_{Ca}$=20 for pure calcium, approximately $Z_{CaH2}\cong 16.04$ for calcium hydride, and approximately $Z_{H2O}\cong 7.428$ for water. The chemical or else biochemical composition of an object can therefore be detected very effectively via the atomic number Z.

Calculation of the atomic number distribution and density distribution in an examination region presupposes at least two X-ray pictures of the region for which the recording geometry is identical but which are compiled by applying X radiation of different energy. When use is made of more than two X-ray pictures recorded with the aid of different X-ray energy, the Z resolution and $\rho$ resolution can be improved, although there is also a consequent increase in the radiation load. Therefore, this possibility does not always apply when a patient is to be examined.

The starting point of the conversion of image data on which attenuation value is based into distribution images of the atomic numbers and of the material or tissue density is knowledge of the isoabsorption lines for each X-ray spectrum of an X-ray apparatus.

As already mentioned, in this case an X-ray spectrum is not to be understood as the narrowly defined term of spectral distribution of an X radiation emitted by the X-ray source of the apparatus, but as a wider term taking account of the different weighting of different spectral regions of the emission spectrum of the X-ray tube on the side of the X-ray detectors. A measured attenuation value is therefore yielded from the direct attenuation of the radiation spectrum emitted by the X-ray tube, and the spectral efficiency of the X-ray detector used. Both values are installation-specific variables and must be determined either directly or indirectly by means of the attenuation values of calibration samples. They are the basis for calculating the isoabsorption lines.

FIG. 3a is a sketch of three example methods 300 for modeling and for calculating a family of isoabsorption lines, specifically a theoretical modeling, an experimental determination and a theoretical modeling with a calibration of the curves by way of experimentally determined parameters.

In principle, there are as many isoabsorption lines to be determined as the number of attenuation values required for covering the span of X-ray attenuations in the X-ray pictures. There is no need in this case to calculate an isoabsorption line for each theoretically occurring attenuation value; isoadsorption lines not calculated can be made available if required by interpolation or other suitable averaging methods.

The basic steps of the theoretical modeling are illustrated in the left-hand branch of the flowchart of FIG. 3a. In step S302, the data of the X-ray emission spectra S(E) specific to an installation are read in with the available tube voltages as parameter. For this purpose, the spectral distributions of the X radiation can be measured experimentally in advance for each individual X-ray installation, or data characteristic of a specific type of X-ray source are used.

The determination of the detector apparatus function w(E) is performed in step S303. Here, as well, an accurate measurement of the detector arrangement can be undertaken in advance, or data characteristic of the detector type such as, for example, the spectral technical specification thereof, are used instead.

The calculation of the isoabsorption lines in the form of families of curves $C_i(\rho,Z)$ or $\mu_i(\rho,Z)$, respectively, is undertaken in step S304 on the basis of a physical model that, for each relative combination of S(E) and w(E) reproduces the X-ray attenuations $C_i$ and $\mu_i$, respectively, for materials with different atomic numbers and in the case of different material densities.

As an alternative to the theoretical modeling of steps S302 to S304, the families of curves of the isoabsorption lines can also be determined experimentally. For this purpose, in step S305 the X-ray attenuations of calibration materials of different density and mean atomic number are measured in the X-ray apparatus for different relevant combinations of S(E) and w(E). The measured values form the interpolation points for the following calculation of the families of curves of isoabsorption lines $C_i$ to $\mu_i$, respectively, in step S306.

As a further alternative, the families of curves $C_i$ and $\mu_i$, respectively, modeled on a theoretical basis can be calibrated with the aid of experimentally determined X-ray attenuation values. The attenuation values required for calibrating the theoretical families of curves are measured in step S307, as described above for step S305, with the aid of suitable calibration materials or phantoms in the X-ray installation.

By contrast with the purely theoretical modeling of steps S302 to S304, is not an exact knowledge of the X-ray emission spectra S(E) and w(E) that is a presupposition in this method, but rather parameters of the theoretical modeling of the families of curves of isoabsorption lines $C_i$ and $\mu_i$, respectively, in step S308. Finally, the calibration of the curves in step S309 with the aid of calibration values determined experimentally in step S307 defines values for these parameters that are specific to the X-ray emission spectra and detector apparatus functions of the X-ray apparatus.

The determination of the isoabsorption lines for the required X-ray attenuation values and combinations of S(E) and w(E) provide the presuppositions for a transformation of image data, which represent attenuation values of the X-radiation upon passage through a tissue, into image data that represent a distribution of the atomic number or the material density in the relevant tissue.

The three example methods for determining isoabsorption lines can also be used in a mixed fashion depending on the task. For example, values which can be determined experimentally only inprecisely or only at great expense, or even cannot be determined at all, can be supplemented or have their accuracy rendered more precise with the aid of theoretical modeling. Data uncovered with different methods are then combined in step S310 to form a uniform data record, and are held ready for the image transformations in step S311.

FIG. 3b illustrates a transformation method 320 suitable for the method according to at least one embodiment of the invention. At least one embodiment of the method is based on the families of curves of isoabsorption lines determined using one of the above-described methods 300 and held ready as data record in step S321.

A pixelwise transformation is performed. A transformation of an X-ray attenuation value distribution based on two X-ray images recorded for different X-ray energy spectra but identical recording geometry is assumed below. This is the minimum presupposition for carrying out a transformation according to at least one embodiment of the invention. However, it is also possible to use more than two X-ray pictures in conjunction with more than two different energy distributions of the X-radiation.

The pixels to be transformed are selected in step S322, and the attenuation values $C_1$ and $\mu_1$, respectively, for this pixel are read in the following step S323 from the first X-ray image, and $C_2$ and $\mu_2$, respectively are read from the second X-ray image. The interrogation of the X-ray spectrum $S_1(E)$ used for the first X-ray picture, and of the detector apparatus functions $w_1(E)$ as well as of the corresponding values $S_2(E)$ and $w_2(E)$ for the second X-ray image is performed in the subsequent step S324.

These values form the parameters of a subsequent selection of the isoabsorption lines to be assigned to the respective attenuation values. The spectral distributions $S_i(E)$ and $w_i(E)$, respectively, can also be determined here indirectly, for example via an interrogation of the X-ray voltages $U_1$ or $U_2$, respectively, that are used, or of the operating parameters of the X-ray detectors.

A first curve, which fulfils the conditions $C_1$ and $\mu_1$, respectively, for the parameters $S_1(E)$ and $w_1(E)$, and a second curve, which fulfils the conditions $C_2$ and $\mu_2$, respectively, for the parameters $S_2(E)$ and $w_2(E)$ are selected in step S325 from the data record, held ready in step S321, of isoabsorption lines. An example of a first isoabsorption line 11 obtained in such a way, and of a second 41 isoabsorption line is illustrated in FIG. 4.

The point of intersection 42 as intersection set of the two curves 11 and 41 is calculated in step S326. The curve intersection 42 can be determined, for example, by local linear transformation or by finding the point of intersection iteratively. Since the two curves 11 and 41 represent two different attenuation values for the same pixel and therefore for an identical subregion of a tissue being examined, two attenuation values must be caused by the same type of material or tissue. The coordinates ($\rho$, Z) of the curve intersection point 42 therefore reproduce the material density and the atomic number of the tissue subregion to be assigned to the pixel.

Finally, the atomic number value Z thus determined is written into the atomic number distribution as a corresponding pixel value in step S327, while the determined material density value $\rho$ is similarly written into the density distribution in step S328.

Steps S322 to S328 are repeated for all remaining pixels until a concluding image output can be performed in step S329. It is possible for the step S324 to be skipped in this process, since the spectral distributions $S_i(E)$ and $w_i(E)$, respectively, are identical for all pixels of an image.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A method for imaging examination of an examination object, comprising:
   administering a contrast agent to the examination object;
   thereafter determining at least two spatial distributions of X-ray attenuation values, the X-ray attenuation values representing at least one of a local X-ray attenuation coefficient and a variable linearly dependent thereon, the two spatial distributions including at least, a first attenuation value distribution determined on the basis of a first X-ray spectrum, a second attenuation value distribution determined on the basis of a second X-ray spectrum, differing from the first X-ray spectrum;

evaluating the at least two attenuation value distributions and determining at least one of a spatial distribution of one or more predefined atomic number values and a spatial distribution of non-predefined atomic number values present in the examination object, the spatial distribution including information relating to the distribution of the administered contrast agent in the examination object; and using the spatial atomic number distribution to represent the contrast agent by imaging.

2. The method as claimed in claim 1, wherein an atomic number value of the contrast agent is predefined.

3. The method as claimed in claim 1, wherein the spatial atomic number distribution is determined as a two- or three-dimensional field, the respect field value being a local atomic number value at the location represented by the relevant field.

4. The method as claimed in claim 3, wherein, in addition to the atomic number distribution, a further two- or three-dimensional field is determined whose field values respectively reproduce a local density value.

5. The method as claimed in claim 4, wherein the determined field having the atomic number values and the determined field having the density values are used for the purpose of calculating a local concentration or a local quantity of the contrast agent.

6. The method as claimed in claim 1, wherein a contrast agent having an atomic number greater than 20 is used.

7. The method as claimed in claim 6, wherein a contrast agent having an atomic number greater than 40 is used.

8. The method as claimed in claim 1, wherein a contrast agent having an atomic number less than 83 is used.

9. The method as claimed in claim 1, wherein the contrast agent contains at least one of gadolinium, iodine, ytterbium, dysposium, iron and bismuth.

10. The method as claimed in claim 1, wherein the contrast agent contains an organic compound.

11. The method as claimed in claim 1, wherein the contrast agent contains at least one of an amino acid and a peptide.

12. The method as claimed in claim 1, wherein the contrast agent is designed for selective deposition at least one of at specific sites and in specific tissue parts of the examination object.

13. The method as claimed in claim 1, wherein the contrast agent is added in a weight concentration from the range of $10^{-4}$ to $10^{-7}$.

14. The method as claimed in claim 1, wherein a first functional dependence of a first attenuation value of the first attenuation value distribution of density and atomic number, and at least a second functional dependence of a second attenuation value, assigned to the first attenuation value, of the second attenuation value distribution of density and atomic number are determined, and wherein the spatial atomic number distribution is determined by comparing the first functional dependence with the second functional dependence and, if appropriate, with further functional dependences.

15. The method as claimed in claim 1, wherein a contrast agent having an atomic number less than 70 is used.

16. The method as claimed in claim 1, wherein the contrast agent contains an aliphatic hydrocarbon.

17. The method as claimed in claim 1, wherein the contrast agent is added in a weight concentration from the range of $10^{-5}$ to $10^{-6}$.

18. The method as claimed in claim 1, wherein a first functional dependence of a first attenuation value of the first attenuation value distribution of density and atomic number, and at least a second functional dependence of a second attenuation value, assigned to the first attenuation value, of the second attenuation value distribution of density and atomic number are determined, and wherein the spatial atomic number distribution and a spatial density distribution are determined by comparing the first functional dependence with the second functional dependence and, if appropriate, with further functional dependences.

* * * * *